(12) United States Patent
Usher et al.

(10) Patent No.: US 7,909,762 B2
(45) Date of Patent: Mar. 22, 2011

(54) VEIN HARVESTING SYSTEM INCLUDING DILATOR SHAFT AND REMOVABLE RETRACTOR HOUSING

(75) Inventors: Raymond W. Usher, Coon Rapids, MN (US); Cynthia T. Clague, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1190 days.

(21) Appl. No.: 11/522,866

(22) Filed: Sep. 18, 2006

(65) Prior Publication Data

US 2007/0015970 A1 Jan. 18, 2007

Related U.S. Application Data

(62) Division of application No. 11/147,927, filed on Jun. 8, 2005, now Pat. No. 7,762,951.

(60) Provisional application No. 60/583,004, filed on Jun. 25, 2004.

(51) Int. Cl.
*A61B 17/00* (2006.01)
(52) U.S. Cl. ........................ 600/210; 606/158
(58) Field of Classification Search .................. 606/190, 606/191; 600/164.01, 201, 210, 212, 235
See application file for complete search history.

(56) References Cited

U.S. PATENT DOCUMENTS

| | | | |
|---|---|---|---|
| 4,151,838 A | 5/1979 | Crew | |
| 4,793,346 A | 12/1988 | Mindlich | |
| 4,909,258 A | 3/1990 | Kuntz et al. | |
| 5,013,312 A | 5/1991 | Parins et al. | |
| 5,290,282 A | 3/1994 | Casscells | |
| 5,373,840 A | 12/1994 | Knighton | |
| 5,601,581 A | 2/1997 | Fogarty et al. | |
| 5,653,722 A | 8/1997 | Kieturakis | |
| 5,667,480 A * | 9/1997 | Knight et al. | ............ 600/210 |
| 5,695,514 A | 12/1997 | Chin | |

(Continued)

FOREIGN PATENT DOCUMENTS

WO 2004/006777 1/2004

(Continued)

OTHER PUBLICATIONS

Beckering, et al, "A Method for the Autopsy Study of the Femoral-Popliteal Vessels," Am. J. Clinical Path., 47(5), 1967, 652-653.

*Primary Examiner* — Eduardo C Robert
*Assistant Examiner* — Tara R Carter
(74) *Attorney, Agent, or Firm* — Katharine A. Jackson Huebsch; Mike Jaro

(57) ABSTRACT

The invention provides a system and method for harvesting a vessel section. The system comprises an endoscope, at least one harvesting tool, and an elongated instrument comprising a shaft and a housing. The shaft includes a viewable region along a length of the shaft and a lumen to slidably receive the endoscope. The housing is releasably engaged with the shaft and includes an elongated opening to provide a working area adjacent to a vessel for the harvesting tool. The method includes making an incision at a point corresponding to the proximal end of the vessel section to be harvested. A shaft is inserted through the incision and adjacent to the vessel section. A housing is slidably engaged with the inserted shaft. Harvesting operations are performed in a working area defined by sidewalls of the housing. The harvesting operations are visually monitored through the shaft.

9 Claims, 9 Drawing Sheets

U.S. PATENT DOCUMENTS

| | | |
|---|---|---|
| 5,713,868 A | 2/1998 | Fussman |
| 5,722,934 A | 3/1998 | Knight et al. |
| 5,725,479 A | 3/1998 | Knight et al. |
| 5,730,748 A | 3/1998 | Fogarty |
| 5,730,757 A | 3/1998 | Benetti et al. |
| 5,772,576 A | 6/1998 | Knighton et al. |
| 5,797,946 A | 8/1998 | Chin |
| 5,836,945 A | 11/1998 | Perkins |
| 5,853,417 A | 12/1998 | Fogarty et al. |
| RE36,043 E | 1/1999 | Knighton |
| 5,876,413 A | 3/1999 | Fogarty et al. |
| 5,891,140 A | 4/1999 | Ginn et al. |
| 5,893,858 A | 4/1999 | Spitz |
| 5,899,913 A | 5/1999 | Fogarty et al. |
| 5,902,315 A | 5/1999 | DuBois |
| 5,913,866 A * | 6/1999 | Ginn et al. .............. 606/174 |
| 5,913,870 A | 6/1999 | DeFonzo et al. |
| 5,916,233 A | 6/1999 | Chin |
| 5,922,004 A | 7/1999 | DuBois |
| 5,928,135 A | 7/1999 | Knight et al. |
| 5,928,138 A | 7/1999 | Knight et al. |
| 5,944,736 A | 8/1999 | Taylor et al. |
| 5,967,971 A | 10/1999 | Bolser |
| 5,968,066 A | 10/1999 | Fogarty et al. |
| 5,970,982 A | 10/1999 | Perkins |
| 5,976,171 A | 11/1999 | Taylor |
| 5,980,549 A | 11/1999 | Chin |
| 6,019,720 A | 2/2000 | Bito |
| 6,022,313 A | 2/2000 | Ginn et al. |
| 6,033,361 A | 3/2000 | Co et al. |
| 6,036,714 A | 3/2000 | Chin |
| 6,042,538 A | 3/2000 | Puskas |
| 6,059,802 A | 5/2000 | Ginn |
| 6,068,639 A | 5/2000 | Fogarty et al. |
| 6,071,232 A | 6/2000 | Knighton et al. |
| 6,077,289 A | 6/2000 | Mollenauer |
| 6,110,190 A | 8/2000 | Ginn et al. |
| 6,113,588 A | 9/2000 | Duhaylongsod et al. |
| 6,143,008 A | 11/2000 | Eaves |
| 6,149,584 A | 11/2000 | Raju |
| 6,193,653 B1 | 2/2001 | Evans |
| 6,196,968 B1 | 3/2001 | Rydin |
| 6,203,557 B1 | 3/2001 | Chin |
| 6,206,823 B1 | 3/2001 | Kolata |
| 6,206,899 B1 | 3/2001 | Ginn |
| 6,228,025 B1 | 5/2001 | Hipps et al. |
| 6,277,137 B1 | 8/2001 | Chin |
| 6,319,265 B1 | 11/2001 | Ginn |
| 6,322,499 B1 | 11/2001 | Evans et al. |
| 6,350,236 B1 | 2/2002 | Hipps et al. |
| 6,428,468 B1 | 8/2002 | Knighton et al. |
| 6,436,116 B1 | 8/2002 | Spitz et al. |
| 6,436,118 B1 | 8/2002 | Kayan |
| 6,447,529 B2 | 9/2002 | Fogarty et al. |
| 6,451,035 B1 | 9/2002 | Fogarty et al. |
| 6,453,906 B1 | 9/2002 | Taylor et al. |
| 6,464,701 B1 | 10/2002 | Hooven et al. |
| 6,468,206 B1 | 10/2002 | Hipps et al. |
| 6,478,734 B1 | 11/2002 | Taylor et al. |
| 6,482,153 B1 | 11/2002 | Hipps et al. |
| 6,506,200 B1 | 1/2003 | Chin |
| 6,511,494 B1 | 1/2003 | Knighton et al. |
| 6,551,314 B1 | 4/2003 | Hill et al. |
| 6,558,313 B1 | 5/2003 | Knighton et al. |
| 6,660,016 B2 | 12/2003 | Lindsay |
| 6,740,102 B2 | 5/2004 | Hess et al. |
| 2003/0065349 A1 | 4/2003 | Hess et al. |
| 2004/0092990 A1 | 5/2004 | Opie et al. |
| 2004/0102804 A1* | 5/2004 | Chin .............. 606/190 |
| 2004/0122458 A1 | 6/2004 | Opie et al. |
| 2004/0236214 A1 | 11/2004 | Opie et al. |
| 2004/0267163 A1 | 12/2004 | Opie et al. |
| 2005/0004536 A1 | 1/2005 | Opie et al. |
| 2005/0020940 A1 | 1/2005 | Opie et al. |
| 2005/0021068 A1 | 1/2005 | Opie et al. |
| 2005/0040061 A1 | 2/2005 | Opie et al. |
| 2005/0273125 A1 | 12/2005 | Opie |
| 2005/0283174 A1 | 12/2005 | Opie et al. |
| 2006/0036274 A1 | 2/2006 | Usher et al. |
| 2006/0258996 A1 | 11/2006 | Opie et al. |
| 2007/0005084 A1 | 1/2007 | Clague et al. |
| 2007/0015970 A1 | 1/2007 | Usher et al. |

FOREIGN PATENT DOCUMENTS

| | | |
|---|---|---|
| WO | 2004/105618 | 12/2004 |
| WO | 2004/106203 | 12/2004 |
| WO | 2004/108200 | 12/2004 |
| WO | 2004/110283 | 12/2004 |
| WO | 2004/112881 | 12/2004 |
| WO | 2005/002659 | 1/2005 |
| WO | 2005/004754 | 1/2005 |

* cited by examiner

FIG. 4
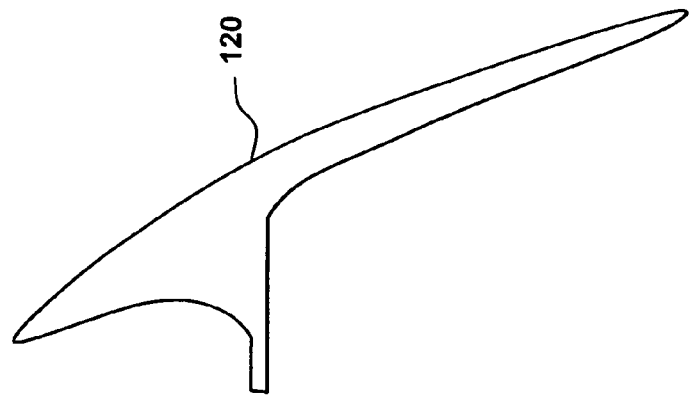
124
122
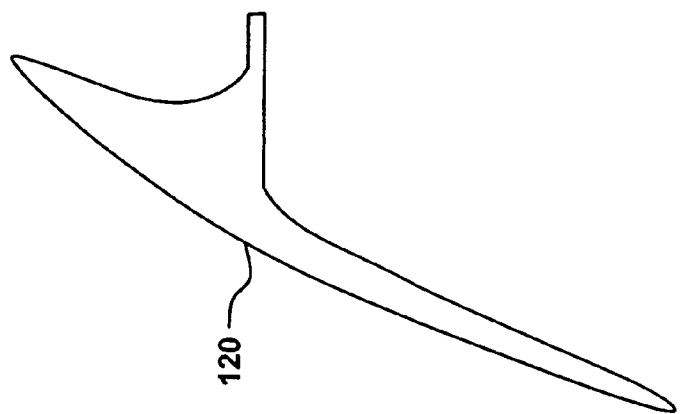

VEIN HARVESTING SYSTEM INCLUDING DILATOR SHAFT AND REMOVABLE RETRACTOR HOUSING

CROSS REFERENCE TO RELATED APPLICATIONS

This application is a divisional of U.S. patent application Ser. No. 11/147,927, filed, Jun. 8, 2005, now U.S. Pat. No. 7,762,951 which claims the benefit of U.S. Provisional Application No. 60/583,004, filed Jun. 25, 2004 (the entire contents of which are incorporated by reference).

TECHNICAL FIELD

This invention relates generally to biomedical systems and methods. More specifically, the invention relates to systems and methods for harvesting a vessel section.

BACKGROUND OF THE INVENTION

Heart disease, specifically coronary artery disease, is a major cause of death, disability, and healthcare expense in the United States and other industrialized countries. A common form of heart disease is atherosclerosis, in which the vessels leading to the heart are damaged or obstructed by plaques containing cholesterol, lipoid material, lipophages, and other materials. When severely damaged or obstructed, one or more of the vessels can be replaced during a coronary artery bypass graft (CABG) procedure. CABG surgery is performed about 350,000 times annually in the United States, making it one of the most commonly performed major operations.

To prevent rejection, the graft material is preferably a blood vessel harvested from elsewhere within a patient's body. The most commonly used bypass vessel is the saphenous vein from the leg. Because the venous system of the leg is redundant, other veins that remain within the patient's leg are adequate to provide return blood flow following removal of the saphenous vein.

Various methods have been used to harvest the saphenous vein. Until recently, the typical procedure involved making a single long incision, extending from a patient's groin to at least the knee and often to the ankle. This method results in substantial postoperative pain, with patients frequently complaining more about discomfort from the site of leg vein harvesting than about their CABG surgery wound. In addition, the extensive incision site is subject to infection and delayed healing, especially in patients with poor circulation, which not infrequently accompanies coronary artery disease. The disfiguring scar from such a large incision is also of concern to some patients.

Less invasive procedures are preferred, and surgical devices and techniques now exist that allow the saphenous vein to be harvested through one or more small, transverse incisions, generally using an endoscope. Endoscopic procedures yield reduced wound complications, reduced discomfort, and superior cosmetic results compared with traditional methods of vein harvesting. Equipment for endoscopic vein harvesting is frequently complex, having multiple parts that are difficult, if not impossible, for one person to manipulate without assistance.

Therefore, it would be desirable to have a system and a method for harvesting a vessel section that overcome the aforementioned and other disadvantages.

SUMMARY OF THE INVENTION

One aspect of the present invention is a device for harvesting a vessel section, e.g., a saphenous vein section. The device comprises a shaft and a housing. The shaft includes a lumen extending from a proximal end of the shaft into a nose portion of the shaft. The shaft further includes a viewable region along a length of the shaft. The housing is releasably engaged with the shaft and includes an elongated opening to provide a working area adjacent to a vessel.

Another aspect of the present invention is a system for harvesting a vessel section, e.g., a saphenous vein section. The system comprises an endoscope, at least one harvesting tool, and an elongated instrument comprising a shaft and a housing. The shaft includes a viewable region along a length of the shaft and a lumen to slidably receive the endoscope. The housing is releasably engaged with the shaft and includes an elongated opening to provide a working area adjacent to a vessel for the harvesting tool.

Yet another aspect of the present invention is a method for harvesting a vessel section, a saphenous vein section. An incision is made in a body at a point corresponding to a proximal end of the vessel section to be harvested. A shaft is inserted through the incision and adjacent to the vessel section. A housing is slidably engaged with the inserted shaft. Harvesting operations are performed in a working area defined by sidewalls of the housing. The harvesting operations are visually monitored through the shaft.

The aforementioned and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

BRIEF DESCRIPTION OF THE DRAWINGS

FIG. 4 is an enlarged cross-sectional view of the housing of FIG. 3;

DETAILED DESCRIPTION OF THE INVENTION

One aspect of the present invention is a device for harvesting a vessel section, e.g., a saphenous vein section. One embodiment of the device, in accordance with the present invention, is illustrated in FIGS. 1-6, in which like elements share like numbers. The figures are not to scale. The device comprises a shaft 110, a housing 120, and a handle 130. Housing 120 removably engages with shaft 110.

Figure 1:
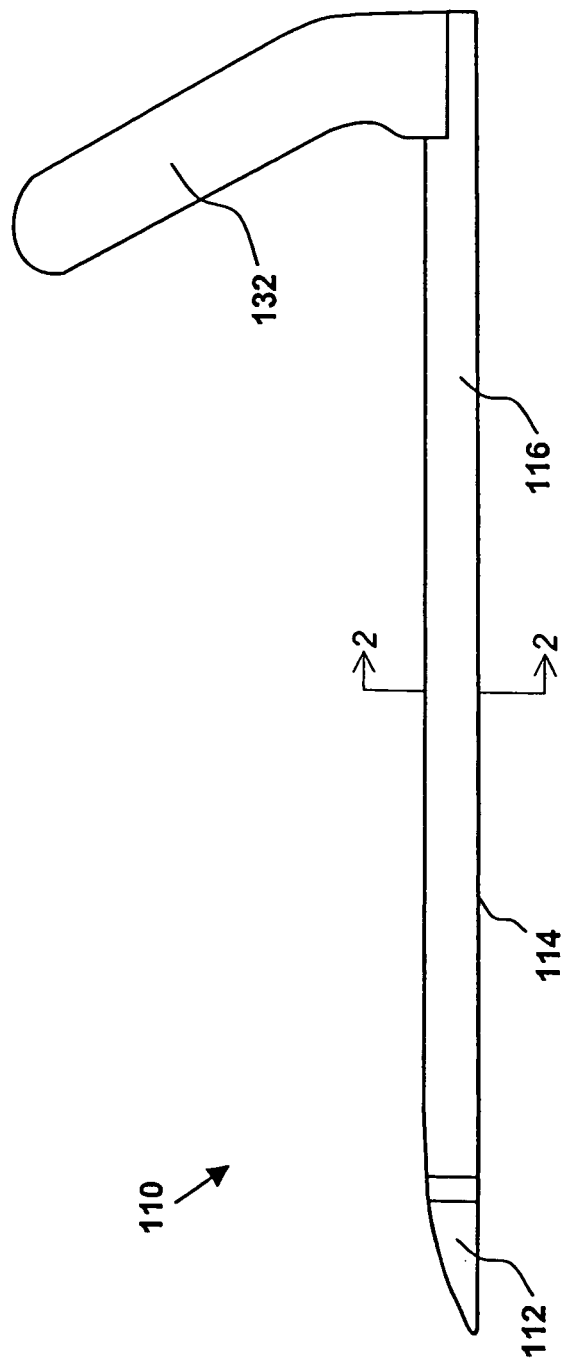
FIG. 1 is an illustration of the shaft of one embodiment of a device for harvesting a vessel section, in accordance with the present invention.
Figure 2:
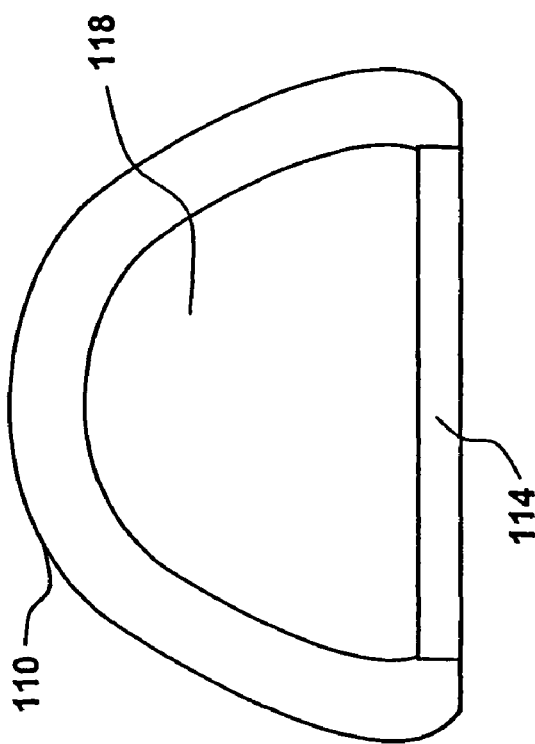
FIG. 2 is an enlarged cross-sectional view of the shaft of FIG. 1.

Shaft 110 is illustrated in FIG. 1, with an enlarged cross-section shown in FIG. 2. Shaft 110 includes a distal nose portion 112 that is used to bluntly dissect tissue away from a vessel being harvested, thereby dilating an area adjacent to the vessel section. As used in this specification, the terms "distal" and "proximal" are with reference to the operator when the device is in use. Nose portion 112 is shown in FIG. 1 to be roughly cone shaped with a spherical tip, however the nose portion 112 may assume alternative shapes that are also acceptable for blunt dissection.

Shaft 110 is made of one or more appropriate biocompatible materials, including, but not limited to, a polymer and/or a metal. For example, shaft 110 may comprise stainless steel. Preferably, at least a portion of shaft 110 comprises a transparent material. In the present embodiment, both nose portion 112 and a bottom portion 114 of shaft 110 are transparent, thus ensuring that regions adjacent to the nose portion and along the length of the shaft are viewable using an instrument such as an endoscope. As illustrated in FIGS. 1 and 2, nose portion 112, bottom portion 114, and body portion 116 are formed individually and assembled to form shaft 110. However, in another embodiment, shaft 110 may be formed as a single, unitary structure, with the entire structure comprising, for example, a transparent material.

Transparent bottom portion 114 is substantially planar and forms a portion of the wall of a lumen 118, as seen in FIG. 2, that extends from a proximal end of shaft 110 into nose portion 112. The shape of lumen 118 may be varied to best accommodate an endoscope. The shape of bottom portion 114 is intended to maximize the optical properties of the portion and may be varied for optimum viewing through the portion.

Figure 3:
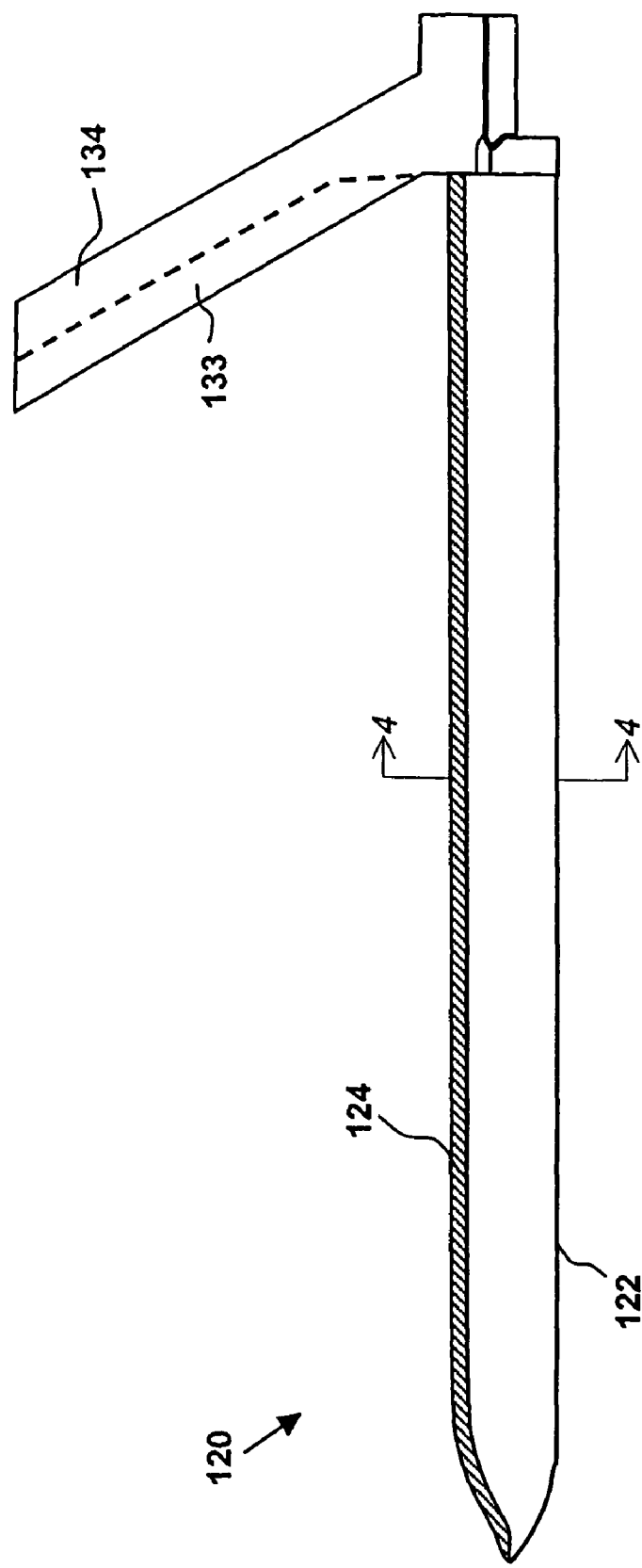
FIG. 3 is an illustration of the housing of one embodiment of a device for harvesting a vessel section, in accordance with the present invention.

Housing 120, illustrated in FIG. 3 and in enlarged cross-section in FIG. 4, comprises one or more appropriate biocompatible materials such as a polymer and/or metal. Housing 120 includes an elongated opening to provide a working area 122 adjacent to a vessel (not shown). Thus, housing 120 acts as a retractor. In the present embodiment, working area 122 extends along the entire length of housing 120 and is defined by the walls of housing 120. As shown in FIG. 4, the walls of housing 120 are curved. In another embodiment, the walls may be straight; however, curved walls can provide a smoother surface for introducing the housing into a body and positioning the housing adjacent to a vessel.

Housing 120 may be connected to a light source (not shown) and transmit light from the light source into the working area. This may be accomplished by, for example, forming housing 120 from a transparent acrylic, including optical fibers within the housing, or lining the housing with an optical lighting film to form a light pipe.

Figure 5:
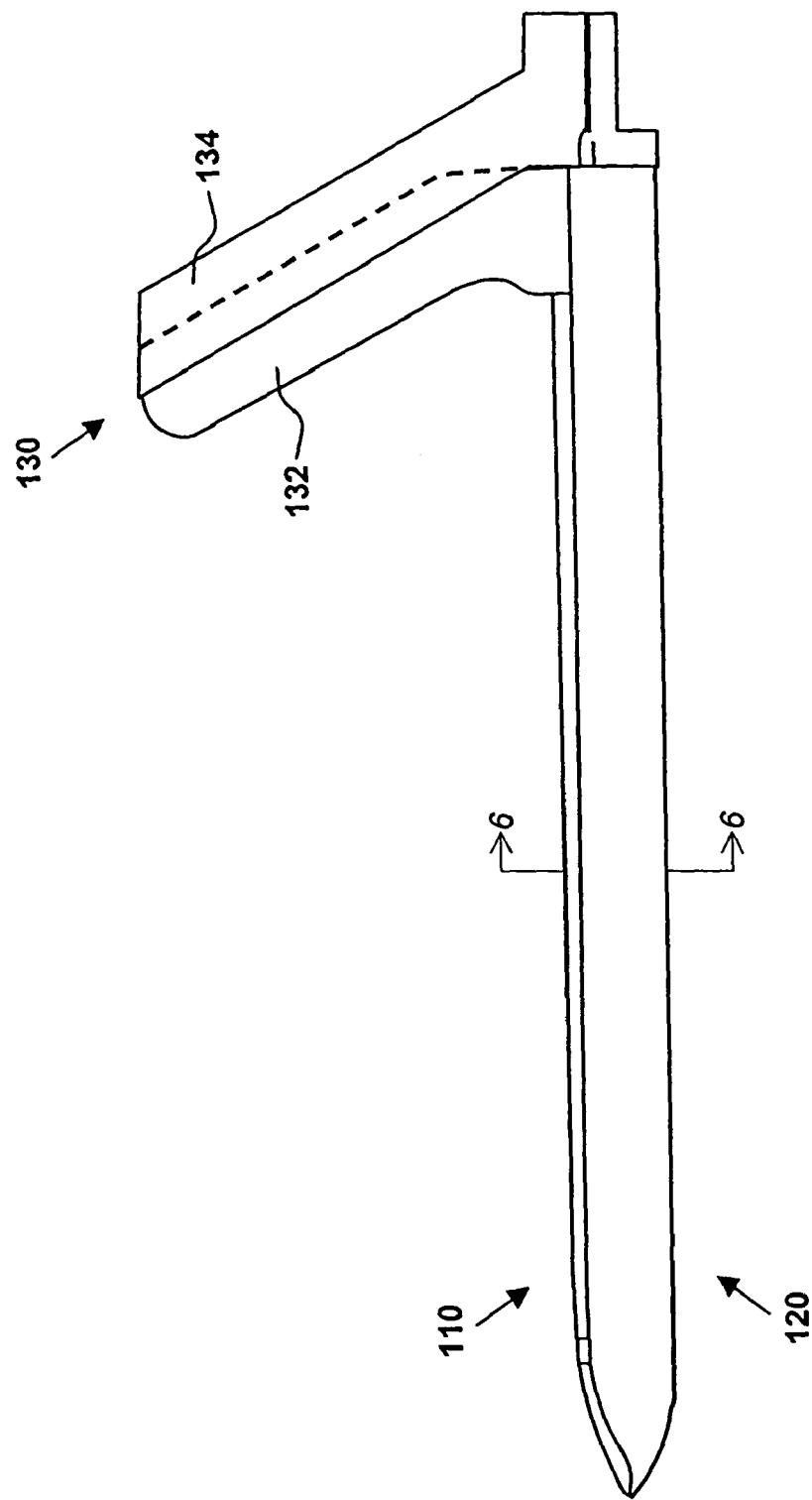
FIG. 5 is an illustration of the shaft of FIG. 1 and the housing of FIG. 3 engaged to form one embodiment of a device for harvesting a vessel section, in accordance with the present invention.

Housing 120 includes an elongated slot 124 that allows housing 120 to be engaged with shaft 110. Slot 124 opens into working area 122. Thus, when housing 120 is engaged with shaft 110, as seen in FIG. 5 and in enlarged cross-section in FIG. 6, an endoscope positioned within shaft lumen 118 can view through the bottom portion 114 of shaft 110 and into working area 122. One or more tabs (not shown) may span slot 124 to provide greater rigidity and structural integrity of housing 120, resulting in slot 124 having more than one opening into working area 122.

Figure 6:
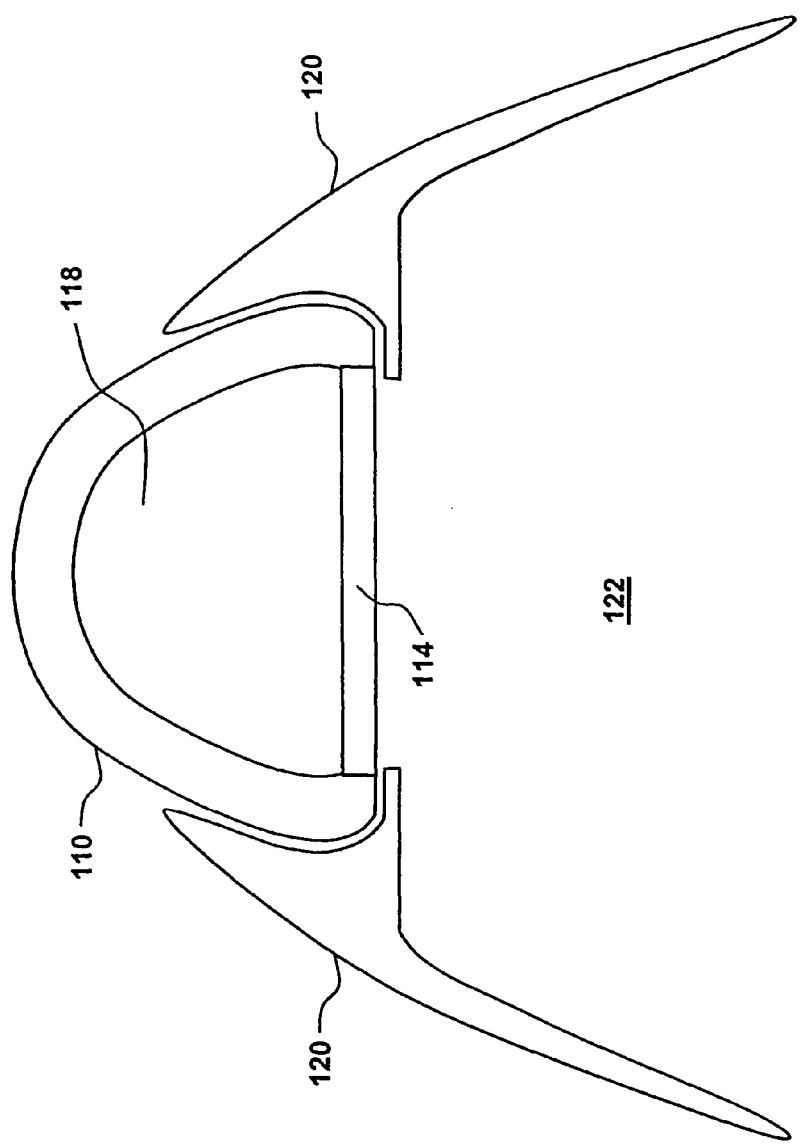
FIG. 6 is an enlarged cross-sectional view of the device of FIG. 5.

The described design allows housing 120 to be engaged with shaft 110, with a portion of shaft 110 received within slot 124 as shown in FIGS. 5 and 6. Housing 120 slides onto shaft 110 at a proximal end of the shaft and is advanced over the shaft toward nose portion 112 until both are positioned as shown in FIG. 5. It will be apparent to one skilled in the art that various other designs for a shaft and housing would permit the housing to be releasably engaged with the shaft. For example, the shaft might include side extensions that are received within grooves in the housing, much like a tongue and groove assembly. In another example, the housing might include individual tabs to engage the shaft.

In the present embodiment, handle 130 is divided into two sections, with handle section 132 (seen in FIGS. 1 and 7) attached to a proximal portion of shaft 110, and handle section 134 (seen in FIGS. 2 and 7) attached to a proximal portion of housing 120. Handle section 134 includes a cavity 133, shown in phantom in FIG. 3, within which a portion of handle section 132 is received as seen in FIG. 5. This design provides a handle that is narrower than the combined widths of the two handle sections when the shaft and housing are engaged and offers the convenience of having a handle on each of shaft 110 and housing 120 when the two elements are separate. In another embodiment, a single handle, for example a removable handle, may be attached to either the shaft or the housing.

Figure 7:
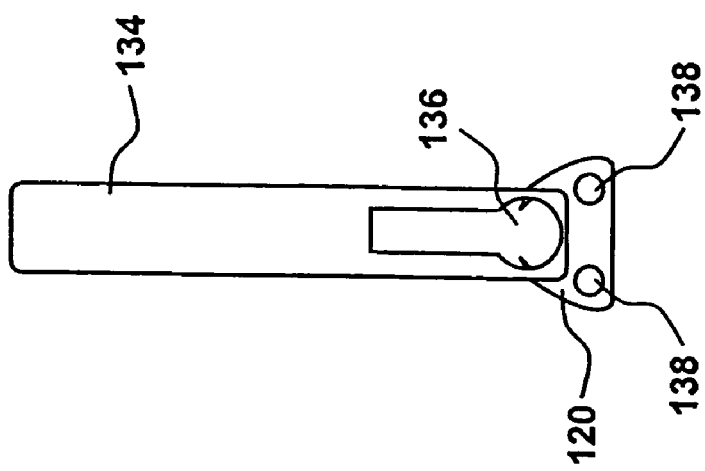
FIG. 7 is a view of the handle section of FIG. 4 seen from its proximal end.

The device includes passageways for an endoscope to be received within lumen 118 and at least one tool to be received within working area 122. The endoscope passageway opens into lumen 118 at the proximal end of shaft 110, while the tool passageway opens into working area 122 at the proximal end of housing 120. Where any portion of the handle would otherwise block these openings, the handle includes endoscope and tool passageways. For example, in the present embodiment, the lower portion of handle section 134 forms a proximal end of housing 120, thereby blocking the opening at the proximal end of housing 120 into working area 122. In addition, the upper portion of handle section 134 is proximal to and, therefore, blocks the opening into lumen 118 when shaft 110 and housing 120 are engaged. To provide openings into lumen 118 and working area 122, handle section 134 includes an endoscope passageway 136 and two tool passageways 138, as can be seen in FIG. 7, which shows handle section 134 viewed from its proximal end. Endoscope passageway 136 provides communication with lumen 118, while tool passageways 138 open into working area 122 to allow harvesting tools access to the area.

Figure 8:
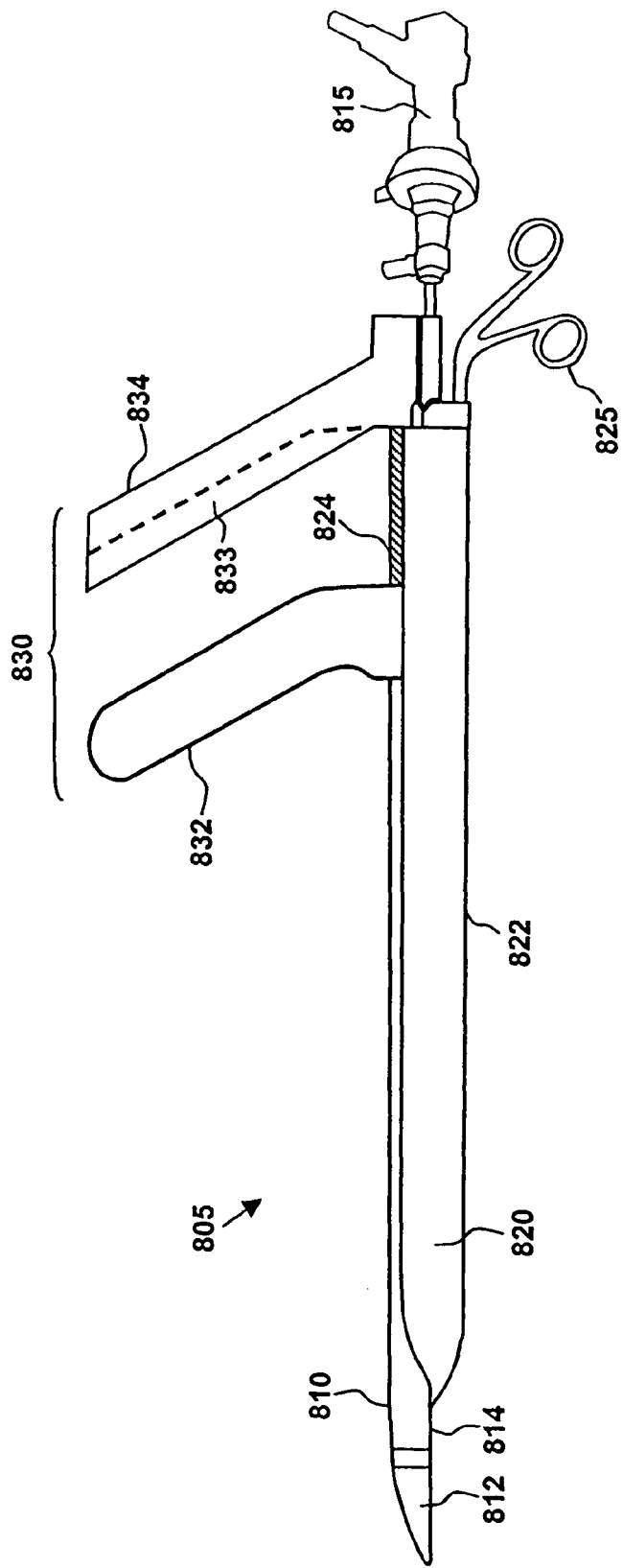
FIG. 8 is an illustration of one embodiment of a system for harvesting a vessel section, in accordance with the present invention.

Another aspect of the present invention is a system for harvesting a vessel section, e.g., a saphenous vein section. One embodiment of the system, in accordance with the present invention, is illustrated in FIG. 8. The system comprises an elongated instrument 805, an endoscope 815, and at least one harvesting tool 825.

Elongated instrument 805 is a device such as has been described in detail above and illustrated in FIGS. 1-7. Elongated instrument 805 comprises a shaft 810, a housing 820, and a handle 830. Shaft 810 is used to dilate an area adjacent to the vessel section being harvested by bluntly dissecting tissue away from the vessel while visually monitoring the process using endoscope 815. Housing 820 provides a working area adjacent to the vessel for the harvesting tool(s) 825. Thus, housing 820 acts as a tissue retractor.

Shaft 810 is made of one or more appropriate biocompatible materials, such as a polymer or a metal, e.g., a stainless steel. Preferably, at least a portion of shaft 810 comprises a transparent material. In the present embodiment, both a distal nose portion 812 and a bottom portion 814 of shaft 810 are transparent to ensure that regions adjacent to the nose portion and along the length of the shaft are viewable using endoscope 815.

Transparent bottom portion 814 is substantially planar and forms a portion of the wall of a lumen (e.g., as seen in FIG. 2 at 118) that extends from a proximal end of shaft 810 into nose portion 812. The lumen is sized to allow endoscope 815 to slide within the lumen for viewing along the length of the shaft through bottom portion 814. Endoscope 815 is, preferably, a four- or five-millimeter (4- or 5-mm), thirty-degree (30°) endoscope; however, other endoscopes may be used in the present invention. The shape of bottom portion 814 is intended to maximize the optical properties of the portion and may be varied in another embodiment.

Housing 820 has an elongated opening that provides a working area 822 for harvesting tool(s) 825 adjacent to the vessel to be harvested. Thus, housing 820 acts as a retractor. Housing 820 may be connected to a light source (not shown) and transmit light from the light source into the working area. This may be accomplished by, for example, forming housing 820 from a transparent acrylic, including optical fibers within the housing, or lining the housing with an optical lighting film to form a light pipe.

In the present embodiment, housing 820 includes a slot 824 that allows housing 820 to be engaged with shaft 810, with a portion of shaft 810 received within slot 824. Slot 824 opens into working area 822. Thus, when housing 820 is engaged with shaft 810, an endoscope positioned within shaft lumen 816 can view through bottom portion 814 of shaft 810 and into working area 822. One or more narrow structures (not shown) may span slot 824 to provide greater rigidity and structural integrity of housing 820.

The described design allows housing 820 to slide onto shaft 810 at a proximal end of the shaft and be advanced over the shaft toward distal nose portion 812. FIG. 8 shows housing 820 partially engaged with shaft 810, with housing 820 capable of sliding further along shaft 810 until the end of the housing is aligned with the end of the shaft as seen in FIG. 6. It will be apparent to one skilled in the art that various other designs for a shaft and housing would permit the housing to be releasably engaged with the shaft, including a tongue and groove design or tabs extending from the housing to engage the shaft.

Handle 830 is divided into two sections, with handle section 832 attached to a proximal portion of shaft 810, and handle section 834 attached to a proximal portion of housing 820. Handle section 834 includes a cavity 833 within which a portion of handle section 832 is received when shaft 810 and housing 820 are fully engaged. This design provides a handle that is narrower than the combined widths of the two handle sections when the shaft and housing are engaged and offers the convenience of having a handle on each of shaft 810 and housing 820 when the two elements are separate. In another embodiment, a single handle, for example a removable handle, may be attached to either the shaft or the housing.

Elongated instrument 805 includes passageways to allow endoscope 815 to be received within lumen 818 and at least one harvesting tool 825 to be received within working area 822. The endoscope passageway may be simply an opening through the proximal end of shaft 810 into the shaft lumen, while the tool passageway may be an opening into working area 822 at the proximal end of housing 820. Where any portion of handle 830 would otherwise block such openings, as is the case in the present embodiment, the handle includes endoscope and tool passageways such as those seen in FIG. 7 at 136 and 138, respectively. As described above, when shaft 810 and housing 820 are engaged, the endoscope passageway is in communication with the shaft lumen, and the tool passageways open into the working area to allow harvesting tools access to the area. A cutting tool 825 is shown in FIG. 8. Other harvesting tools, for example tools to lift or move the vessel being harvested, may be included in the system.

Figure 9:
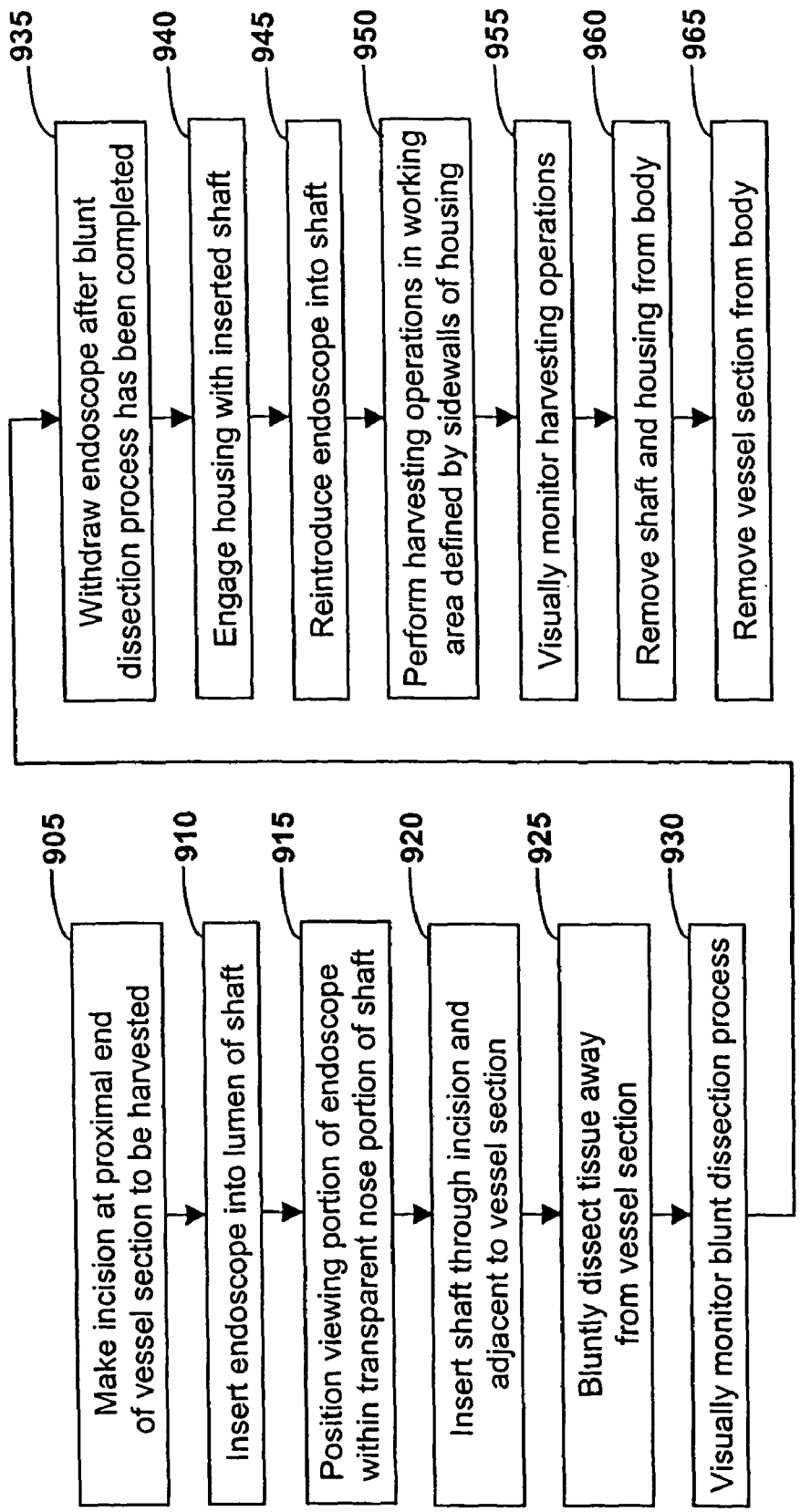
FIG. 9 is a flow diagram of one embodiment of a method for harvesting a vessel section in accordance with the present invention.

Yet another aspect of the present invention is a method for harvesting a vessel section. FIG. 9 shows a flow diagram of one embodiment of the method in accordance with the present invention.

An incision is made in a body at a point corresponding to a proximal end of the vessel section to be harvested (Block 905). An endoscope is inserted into the lumen of a shaft such as is seen in FIG. 1, and the viewing portion of the endoscope is positioned within a transparent nose portion located at the distal end of the shaft (Block 910). The shaft is inserted through the incision and adjacent to the vessel section to be harvested (Block 915). As the shaft is inserted, tissue is bluntly dissected away from the vessel (Block 920). The blunt dissection process is visually monitored using the endoscope (Block 925).

Once the blunt dissection process has been completed, the endoscope is withdrawn from the shaft (Block 930), and a housing such as that seen in FIG. 3 is engaged with the inserted shaft by sliding the housing onto the shaft from the proximal end of the shaft toward the distal nose portion of the shaft (Block 935). The endoscope is then reintroduced into the shaft (Block 940). It will be apparent to one skilled in the art that the housing need not be fully engaged with the shaft in order for the endoscope to be reintroduced into the shaft when using a device such as that seen in FIGS. 1 through 7. One skilled in the art will also recognize that the endoscope need not be removed and reintroduced if the device is designed to accommodate the endoscope while the housing is being engaged with the shaft. For example, the endoscope need not be withdrawn and reintroduced if a two-part handle is designed such that the housing section of the handle can accommodate the endoscope while the housing is being engaged with the shaft or if a single handle is removable.

Harvesting operations such as cutting and cauterizing side branches of the vessel or severing the vessel are performed in a working area defined by sidewalls of the housing (Block 945). The harvesting operations are visually monitored through a transparent bottom portion of the shaft using the endoscope (Block 950). The endoscope can be moved within the shaft lumen to best view the area of operations. Once the harvesting operations have been completed, the shaft and housing are removed from the body (Block 955) as is the harvested vessel (Block 960).

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

What is claimed is:

1. A method for harvesting a vessel section from tissue within a patient's body, the method comprising:
   providing a shaft having a lumen along the length of the shaft, a distal nose portion shaped for dissection of the tissue, and a region along the length of the shaft through which the dissection may be viewed;
   providing a housing having an elongated slot for receiving the shaft, a working area, and an opening between the elongated slot and the working area;
   making an incision in a body at a point corresponding to a proximal end of the vessel section to be harvested;
   inserting the shaft through the incision and adjacent to the vessel section;

engaging the housing with the inserted shaft by sliding the housing onto the inserted shaft;

performing harvesting operations in a working area defined by sidewalls of the housing; and visually monitoring the harvesting operations through the shaft and the housing.

2. The method of claim 1, wherein sliding the housing onto the inserted shaft comprises sliding the housing onto the inserted shaft from the proximal end of the shaft toward a distal nose portion of the shaft.

3. The method of claim 1 further comprising:

inserting an endoscope into a lumen of the shaft; and positioning a viewing portion of the endoscope within a transparent nose portion of the shaft.

4. The method of claim 3 wherein the bottom portion of the shaft is transparent.

5. The method of claim 1 wherein inserting a shaft through the incision and adjacent to the vessel section comprises bluntly dissecting tissue away from the vessel section to be harvested.

6. The method of claim 5 further comprising: visually monitoring the process of bluntly dissecting tissue away from the vessel section to be harvested.

7. The method of claim 1 further comprising: removing the shaft and housing from the body.

8. The method of claim 1 further comprising: removing the vessel section from the body.

9. A method for harvesting a vessel section from tissue within a patient's body, the method comprising:

providing a shaft having a lumen along the length of the shaft, a distal nose portion shaped for dissection of the tissue, a transparent bottom portion, and a region along the length of the shaft through which the dissection may be viewed;

providing a housing having an elongated slot for receiving the shaft, a working area, and an opening between the elongated slot and the working area;

making an incision in a body at a point corresponding to a proximal end of the vessel section to be harvested;

inserting an endoscope into a lumen of the shaft and positioning a viewing portion of the endoscope within a transparent nose portion of the shaft;

inserting the shaft through the incision and adjacent to the vessel section;

engaging the housing with the inserted shaft;

performing harvesting operations in a working area defined by sidewalls of the housing;

visually monitoring the harvesting operations through the shaft and the housing withdrawing the endoscope from the lumen of the shaft;

reinserting the endoscope into the lumen of the shaft; and visually monitoring the harvesting operations through the transparent bottom portion of the shaft.

\* \* \* \* \*